(12) United States Patent
Moon et al.

(10) Patent No.: US 9,236,573 B2
(45) Date of Patent: Jan. 12, 2016

(54) ORGANIC SEMICONDUCTOR COMPOUND, METHOD FOR PREPARING SAME, AND ORGANIC SEMICONDUCTOR DEVICE EMPLOYING SAME

(75) Inventors: Sang Jin Moon, Daejeon (KR); Jong Cheol Lee, Daejeon (KR); Won Suk Shin, Seoul (KR); Sang Kyu Lee, Daejeon (KR)

(73) Assignee: KOREA RESEARCH INSTITUTE OF CHEMICAL TECHNOLOGY

( * ) Notice: Subject to any disclaimer, the term of this patent is extended or adjusted under 35 U.S.C. 154(b) by 133 days.

(21) Appl. No.: 14/114,065

(22) PCT Filed: Apr. 26, 2012

(86) PCT No.: PCT/KR2012/003230
§ 371 (c)(1),
(2), (4) Date: Oct. 25, 2013

(87) PCT Pub. No.: WO2012/148185
PCT Pub. Date: Nov. 1, 2012

(65) Prior Publication Data
US 2014/0046013 A1    Feb. 13, 2014

(30) Foreign Application Priority Data

Apr. 27, 2011 (KR) .................. 10-2011-0039597
Apr. 25, 2012 (KR) .................. 10-2012-0043437

(51) Int. Cl.
*H01L 51/00* (2006.01)
*C07D 495/04* (2006.01)

(52) U.S. Cl.
CPC .......... *H01L 51/0074* (2013.01); *C07D 495/04* (2013.01); *H01L 51/0036* (2013.01)

(58) Field of Classification Search
CPC .............. C07D 495/04; H01L 51/0036; H01L 51/0074
USPC .................... 526/256, 257; 549/42
See application file for complete search history.

(56) References Cited

FOREIGN PATENT DOCUMENTS

| JP | 1999-195790 A | 7/1999 | |
|---|---|---|---|
| JP | 2006216814 A | 8/2006 | |
| JP | 2007-067262 A | 3/2007 | |
| JP | 2010180151 A * | 8/2010 | ........... C07D 333/50 |
| KR | 1020100098293 A | 9/2010 | |
| WO | 2010/058692 A1 | 5/2010 | |

OTHER PUBLICATIONS

Loser et al. (A Naphthodithiophene-Diketopyrrolopyrrole Donor Molecule for Efficient Solution-Processed Solar Cells, J. Am. Chem. Soc., 2011, 133 (21), pp. 8142-8145, Publication Date (Web): May 5, 2011).*
Osaka, Itaru, "Impact of Isomeric Structures on Transistor Performances in Napthodithiophene Semiconducting Polymers", Journal of the American Chemical Society, Apr. 8, 2011, pp. 6852-6860.
Extended European Search Report Appln. No. PCT/KR2012003230; Issued Sep. 30, 2014.
Veaceslav Coropceanu, et al; "Vibronic Coupling in Organic Semiconductors: The Case of Fused Polycyclic Benzene-Thiophene Sructures", Chem. Eur. J. vol. 12, pp. 2073-2080; Feb. 20, 2008.
International Search Report mailed Dec. 3, 2012; PCT/KR2012/003230.

* cited by examiner

*Primary Examiner* — Ling Choi
*Assistant Examiner* — Chun-Cheng Wang
(74) *Attorney, Agent, or Firm* — Ladas & Parry LLP

(57) ABSTRACT

Provided are an organic semiconductor compound, a method for preparing same, a polymer compound having the organic semiconductor compound of the present invention as a monomer, and an organic semiconductor device containing the polymer compound. Said organic semiconductor compound has side chains in the chemical structure thereof, and is highly soluble in a solvent, and therefore the organic semiconductor compound can be effectively used in solution-based processes. The organic semiconductor device containing the polymer compound according to the present invention yields high manufacturing efficiency.

13 Claims, 1 Drawing Sheet

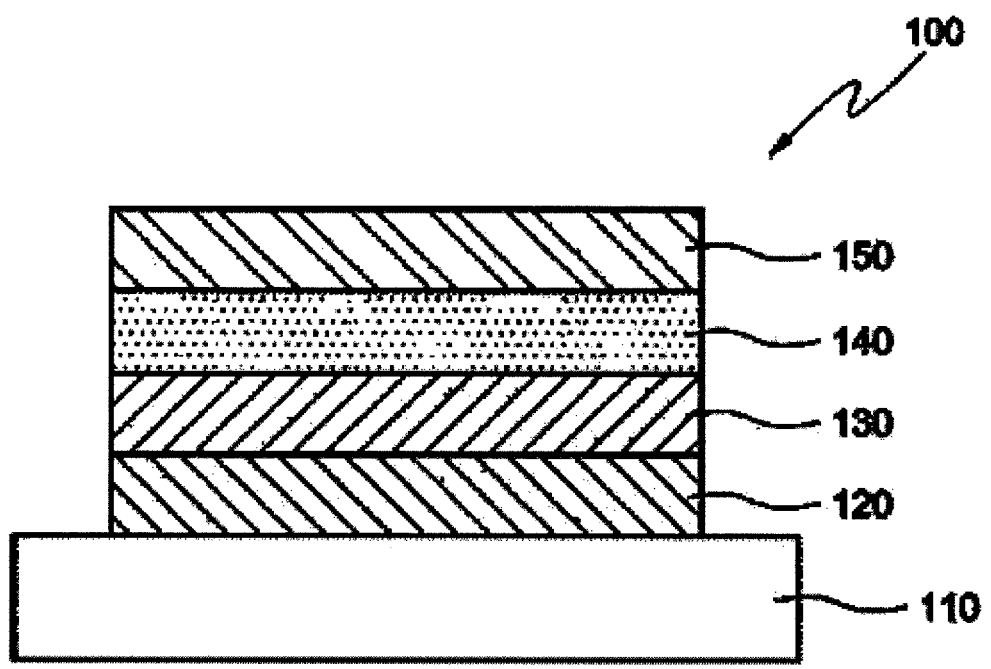

ORGANIC SEMICONDUCTOR COMPOUND, METHOD FOR PREPARING SAME, AND ORGANIC SEMICONDUCTOR DEVICE EMPLOYING SAME

TECHNICAL FIELD

The present invention relates to an organic semiconductor compound and uses thereof. More particularly, the present invention relates to an organic semiconductor compound having high solubility and charge mobility as an organic semiconductor compound, which is a material capable of being used in an organic semiconductor device, and uses thereof.

BACKGROUND ART

Since a device using an organic semiconductor does not require particular film forming conditions as compared to an inorganic semiconductor device according to the related art, this device may form a semiconductor thin film on various substrates or form a film at room temperature, such that this device is expected to decrease cost or implement flexibility by forming a thin film on a polymer film, or the like.

An organic semiconductor material has been widely used in devices or apparatus including, for example, an organic field-effect transistor (OFET), an organic light emitting diode (OLED), a photo detector, a photovoltaic (PV), a sensor, a memory device, and a logical circuit.

In order to manufacture a more various and cheap electronic device, organic semiconductor materials have been developed. Currently, as the organic semiconductor material, polyacene compounds such as anthracene, tetracene, pentacene, and the like, have been widely studied together with polyphenylenevinylene, polypyrrole, polythiophene, and oligothiophene. In these polyacene compounds, as a length of a chain is extended, a π system is widened, and a large orbital overlap is formed between molecules adjacent to each other, such that charge mobility is expected to be improved.

Meanwhile, among organic compounds having high charge mobility, a compound having a benzene-thiophene fused ring and a naphthalene-thiophene fused ring has been suggested, but it is difficult to introduce thiophene in naphthalene through organic synthesis, such that the compound having the naphthalene-thiophene fused ring is not a real material, but only a synthesizable structure thereof has been mentioned (Chem. Eur. J., 2006, 12, 2037-2080).

Recently, among the compounds having this naphthalene-dithiophene fused ring, a compound having the following structure has been disclosed in International Patent Laid-Open Publication No. WO 2010-058692, but solubility and electric properties may be also limited due to limitation in a substituent substituted in a moiety of the naphthalene-dithiophene fused ring, which is a factor capable of affecting physical properties of the material, or the like.

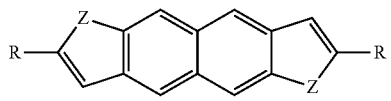

[In Chemical Formula, Z is S or Se, and R is one selected from hydrogen, an alkyl group, and a phenyl group.]

Meanwhile, since most of the polyacene compounds require high crystalline structure in order to provide molecular orientation causing excellent charge mobility and are slightly insoluble in a general solvent, most of the polyacene compounds have been vapor-deposited. This vapor deposition is expensive and requires a complicated apparatus, such that development of an organic semiconductor material suitable for a solution-based process capable of decreasing amounts of materials used in production and consumed energy has been demanded.

Therefore, in the present invention, a compound having a naphthalene-dithiophene fused ring having excellent charge mobility, and including various substituents introduced at 4,9-positions of the compound to thereby be advantageous for polymer synthesis through polymerization, and having high solubility to thereby be advantageous for the solution-based process, and a polymer compound containing this compound as a monomer was synthesized.

DISCLOSURE

Technical Problem

An object of the present invention is to provide a new organic semiconductor compound having high solubility and charge mobility.

Another object of the present invention is to provide a method for synthesizing the new organic semiconductor compound as described above.

Still another object of the present invention is to provide a polymer compound including the organic semiconductor compound according to the present invention as a monomer.

Still another object of the present invention is to provide an organic semiconductor device containing the polymer compound according to the present invention.

Technical Solution

The present invention relates to an organic semiconductor compound, a method for preparing the same, a polymer compound including the organic semiconductor compound according to the present invention as a monomer, and an organic semiconductor device containing this polymer compound. More particularly, the present invention relates to an organic semiconductor compound used as a material of an organic semiconductor device, having a side chain to thereby have high solubility, and having a naphthalene-dithiophene fused ring to thereby have high charge mobility, a method for preparing the same, a polymer compound including the organic semiconductor compound according to the present invention as a monomer, and an organic semiconductor device containing this polymer compound.

In one general aspect, there is provided an organic semiconductor compound represented by the following Chemical Formula 1.

[Chemical Formula 1]

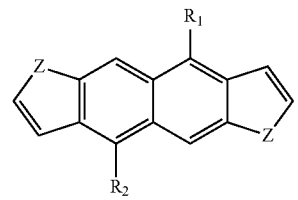

[In Chemical Formula 1, Z is S or Se; and $R_1$ and $R_2$ each are independently $(C_1$-$C_{20})$alkyl, $(C_1$-$C_{20})$alkoxy, $(C_1$-$C_{20})$alkylthio, or $(C_6$-$C_{70})$ar$(C_1$-$C_{20})$alkyl, and the alkyl and aralkyl may be further substituted with at least one substituent selected from $(C_1-C_{20})$alkyl, $(C_2-C_{20})$alkenyl, $(C_2-C_{20})$alkynyl, $(C_1-C_{20})$alkoxy, amino groups, hydroxyl groups, halogen groups, cyano groups, nitro groups, trifluoromethyl groups, and silyl groups.]

Preferably, in the organic semiconductor compound of Chemical Formula 1, $R_1$ and $R_2$ each may be independently $(C_1-C_{20})$alkyl or $(C_1-C_{20})$alkoxy.

In addition, in the organic semiconductor compound of Chemical Formula 1, Z may be S.

As disclosed herein, the terms ⌐alkyl⌐, ⌐alkoxy⌐, and other substituents including a ⌐alkyl⌐ part include both of the straight chain type and the branched chain type. In addition, the term ⌐aryl⌐ described herein, which is an organic radical derived from aromatic hydrocarbon by removing one hydrogen atom therefrom, may include a single ring or a fused ring containing, properly 4 to 7 ring atoms, and preferably 5 or 6 ring atoms, and include rings in which two or more aryls are combined through single bond(s). A specific example of aryl may include phenyl, naphthyl, biphenyl, anthryl, indenyl, fluorenyl, and the like, but is not limited thereto. The term ⌐heteroaryl⌐ described herein may mean an aryl group containing 1 to 4 hetero atom(s) selected from B, N, O, S, P(=O), Si, and P for the aromatic cyclic backbone atoms, and carbon atom(s) for remaining aromatic cyclic backbone atoms. The heteroaryl may be a 5- or 6-membered monocyclic heteroaryl or a polycyclic heteroaryl which is fused with one or more benzene ring(s), and may be partially saturated. In addition, the heteroaryl in the present invention may include the structures having one or more heteroaryl group(s) bonded through a single bond.

In another general aspect, there is provided a method for preparing an organic semiconductor compound represented by Chemical Formula 1, the method including: introducing a protective group in a compound represented by the following Chemical Formula 2 to prepare a compound represented by Chemical Formula 3;

halogenating the compound represented by the following Chemical Formula 3 to prepare a compound represented by the following Chemical Formula 4;

reacting the compound represented by the following Chemical Formula 4 with a compound represented by the following Chemical Formula 5 to prepare a compound represented by the following Chemical Formula 6; and preparing the compound represented by Chemical Formula 1 from the compound represented by the following Chemical Formula 6.

[Chemical Formula 2]

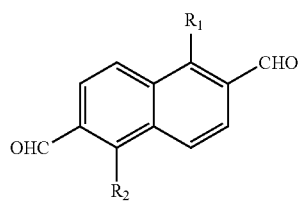

[Chemical Formula 3]

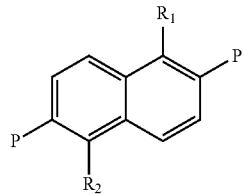

[Chemical Formula 4]

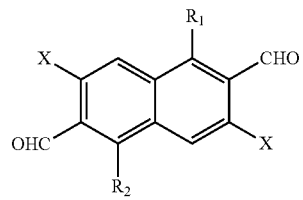

[Chemical Formula 5]

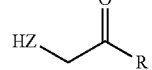

[Chemical Formula 6]

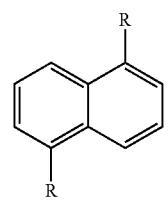

[In Chemical Formulas 1 to 6,
z is S or Se;
$R_1$ and $R_2$ each are independently $(C_1-C_{20})$alkyl, $(C_1-C_{20})$alkoxy, $(C_1-C_{20})$alkylthio, or $(C_6-C_{20})$ar$(C_1-C_{20})$alkyl, and the alkyl and aralkyl may be further substituted with at least one substituent selected from $(C_1-C_{20})$alkyl, $(C_2-C_{20})$alkenyl, $(C_2-C_{20})$alkynyl, $(C_1-C_{20})$alkoxy, amino groups, hydroxyl groups, halogen groups, cyano groups, nitro groups, trifluoromethyl groups, and silyl groups;
P is a protective group; and
R is hydroxyl or $(C_1-C_{20})$alkoxy.]

In addition, a compound represented by the following Chemical Formula 8 may be prepared from a compound represented by the following Chemical Formula 7, and the compound represented by the Chemical Formula 2 may be prepared from a compound represented by the following Chemical Formula 8 again.

[Chemical Formula 7]

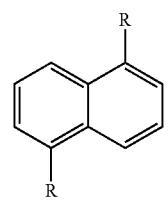

[Chemical Formula 8]

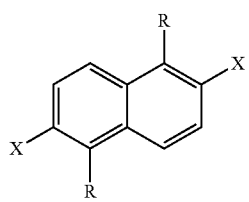

[In Chemical Formulas 7 and 8,
Z is S or Se; and
R is hydroxyl or $(C_1-C_{20})$alkoxy.]

At the time of introducing a protective group protecting an aldehyde group of the compound represented by Chemical Formula 2 to prepare the compound represented by Chemical Formula 3, the protective group is not particularly limited, but one selected from N,N-dimethylethylenediamine, 1,3-propanediol, 1,3-propanedithiol, and pinacol may be used.

At the time of preparing the compound represented by Chemical Formula 4 from the compound represented by Chemical Formula 3 using a halogenating agent, the halogenating agent is not particularly limited, but one selected from bromine, chlorine, N-bromosuccinimide, and 1,2-dibromotetrachloroethane may be used.

In addition, a method for introducing several substituents in $R_1$ of Chemical Formula 1 according to the present invention is not particularly limited, but several substituents may be firstly introduced in $R_1$ of a naphthalene backbone and then fused with a thiophene ring, or after the naphthalene backbone may be fused with the thiophene ring, and several substituents may be introduced in $R_1$.

Further, preferably, in the compound represented by Chemical Formula 1, Z may be S, and R may be $(C_1-C_{20})$ alkoxy.

In another general aspect, there is provided a polymer compound including an organic semiconductor compound represented by Chemical Formula 1 as a monomer.

The polymer compound according to the exemplary embodiment of the present invention may be represented by the following Chemical Formula 11.

[Chemical Formula 11]

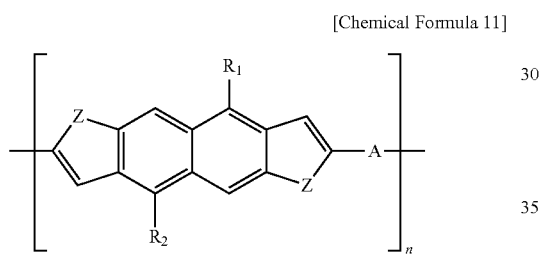

[In Chemical Formula 11,
A is $(C_6-C_{20})$arylene or $(C_3-C_{20})$heteroarylene,
Z is S or Se;
$R_1$ and $R_2$ each are independently $(C_1-C_{20})$alkyl, $(C_1-C_{20})$alkoxy, $(C_1-C_{20})$alkylthio, or $(C_6-C_{20})$ar$(C_1-C_{20})$alkyl, and the alkyl and aralkyl may be further substituted with at least one substituent selected from $(C_1-C_{20})$alkyl, $(C_2-C_{20})$alkenyl, $(C_2-C_{20})$alkynyl, $(C_1-C_{20})$alkoxy, amino groups, hydroxyl groups, halogen groups, cyano groups, nitro groups, trifluoromethyl groups, and silyl groups; and
n is an integer of 1 to 500.]

In Chemical Formula 11 according to the exemplary embodiment of the present invention, A is an arylene or heteroarylene compound, and any compound may be used as long as the compound may provide a divalent bond and be an electron acceptor compound. More specifically, A may be at least one selected from compounds having the following structures.

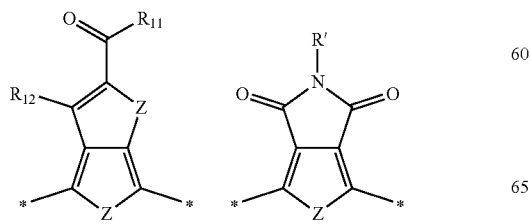

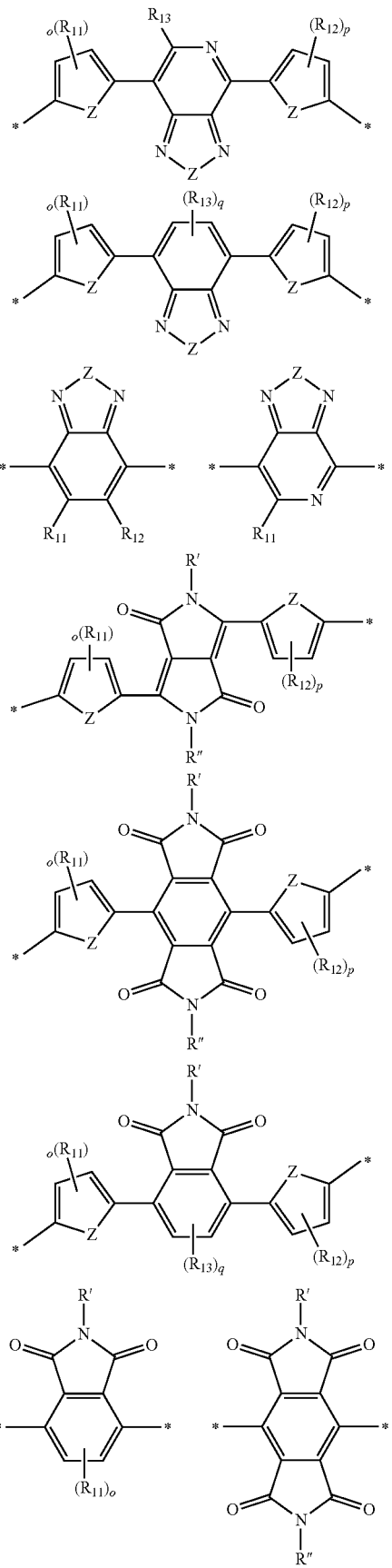

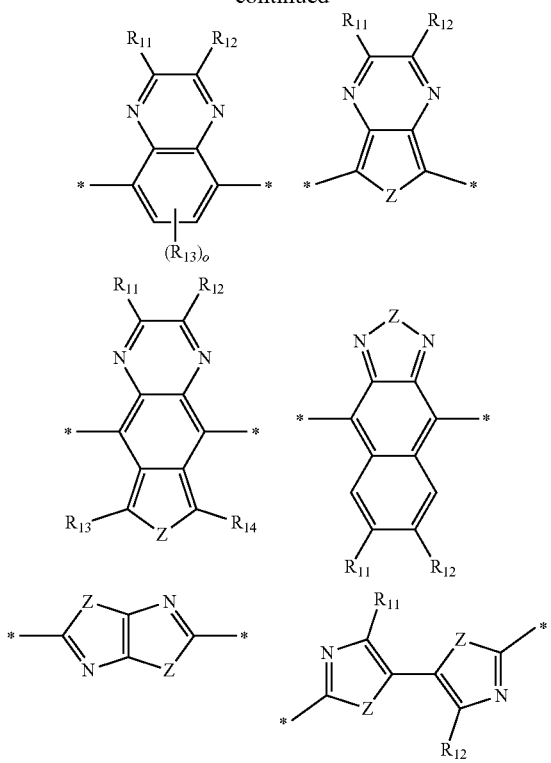

[In Structural Formula,

Z is S or Se,

R' and R" each are independently hydrogen, $(C_1-C_{20})$alkyl, $(C_6-C_{20})$aryl, $(C_3-C_{20})$ heteroaryl, or $(C_6-C_{20})$ar$(C_1-C_{20})$alkyl, $R_{11}$ to $R_{14}$ each are independently hydrogen, halogen, $(C_1-C_{20})$alkyl, $(C_1-C_{20})$alkoxy, or $(C_6-C_{20})$ar$(C_1-C_{20})$alkyl, the alkyl, aryl, heteroaryl, and aralkyl of R' and R" and the alkyl, alkoxy, and aralkyl of $R_{11}$ to $R_{14}$ may be further substituted with at least one substituent selected from $(C_1-C_{20})$alkyl, $(C_2-C_{20})$alkenyl, $(C_2-C_{20})$alkynyl, $(C_1-C_{20})$alkoxy, amino groups, hydroxyl groups, halogen groups, cyano groups, nitro groups, trifluoromethyl groups, and silyl groups; and o, p, and q are integers of 1 to 2.]

The polymer compound according to the exemplary embodiment of the present invention may be selected from compounds represented by the following Structural Formulas, but is not limited thereto.

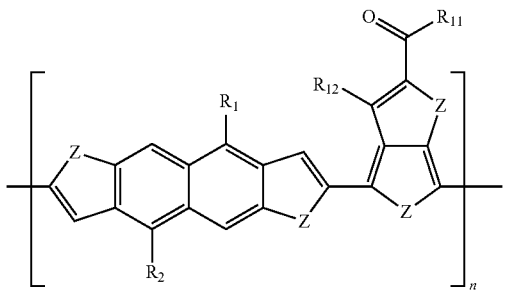

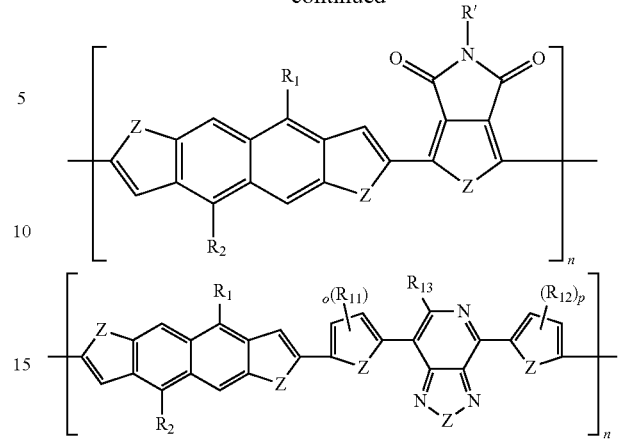

[In Structural Formula,

Z is S or Se, $R_1$ and $R_2$ each are independently $(C_1-C_{20})$alkyl, $(C_1-C_{20})$alkoxy, $(C_1-C_{20})$alkylthio, or $(C_5-C_{20})$ar$(C_1-C_{20})$alkyl, and the alkyl and aralkyl may be further substituted with at least one substituent selected from $(C_1-C_{20})$alkyl, $(C_2-C_{20})$alkenyl, $(C_2-C_{20})$alkynyl, $(C_1-C_{20})$alkoxy, amino groups, hydroxyl groups, halogen groups, cyano groups, nitro groups, trifluoromethyl groups, and silyl groups;

R' is hydrogen, $(C_1-C_{20})$alkyl, $(C_6-C_{20})$aryl, $(C_3-C_{20})$heteroaryl, or $(C_6-C_{20})$ar$(C_1-C_{20})$alkyl, $R_{11}$ to $R_{13}$ each are independently hydrogen, halogen, $(C_1-C_{20})$alkyl, $(C_1-C_{20})$alkoxy, or $(C_6-C_{20})$ar$(C_1-C_{20})$alkyl, the alkyl, aryl, heteroaryl, and aralkyl of R' and the alkyl, alkoxy, and aralkyl of $R_{11}$ to $R_{13}$ may be further substituted with at least one substituent selected from $(C_1-C_{20})$alkyl, $(C_2-C_{20})$alkenyl, $(C_2-C_{20})$alkynyl, $(C_1-C_{20})$alkoxy, amino groups, hydroxyl groups, halogen groups, cyano groups, nitro groups, trifluoromethyl groups, and silyl groups;

n is an integer of 1 to 500; and o and p are integers of 1 to 2.]

In another general aspect, there is provided an organic semiconductor device containing a polymer compound prepared according to the present invention.

Advantageous Effects

An organic semiconductor compound according to the present invention may have high solubility as well as charge mobility by having side chains at 4,9-positions of a naphthalene-dithiophene fused ring, such that there are advantages in that the organic semiconductor compound may be applied to solution-based processes and used to synthesize a polymer as a monomer.

Since an organic semiconductor device containing the polymer compound according to the present invention has the naphthalene-dithiophene fused ring, the organic semiconductor device may have high charge mobility and solubility, thereby having excellent efficiency and performance.

DESCRIPTION OF DRAWINGS

FIG. 1 is a mimetic diagram showing an example of an organic photoelectronic device prepared according to the present invention (100: organic photoelectronic device, 110:

substrate, 120: first electrode, 130: buffer layer, 140: photoelectric conversion layer, and 150: second electrode).

BEST MODE

The present invention will be understood and appreciated more fully from the following Examples, and the Examples are for illustrating the present invention and not for limiting the present invention.

Example 1

Synthesis of 4,9-bis(2-ethylhexyloxy)-1,6-dithiadicyclopenta[b,g]naphthalene

Synthesis of 1,5-bis-(2-ethylhexyloxy)naphthalene

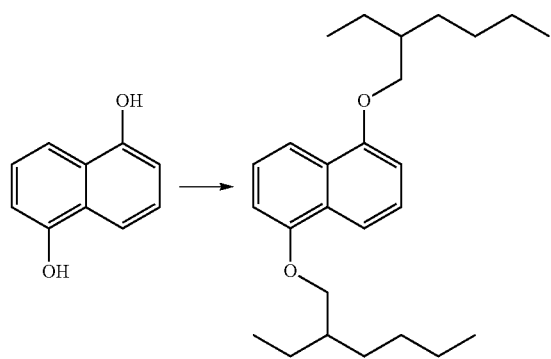 [SMILES: Oc1cccc2c(O)cccc12 ; CCCCC(CC)COc1cccc2c(OCC(CC)CCCC)cccc12]

5.0 g of 1,5-dihydroxynaphthalene (31.2 mmol) and 43.1 g of potassium carbonate (311 mmol) were dissolved in 50 mL of dimethylformamide (DMF). 18.0 g of 2-ethylhexyl bromide (93.2 mmol) was added thereto and stirred at 1000 for 24 hours. After the mixture was quenched with water, extracted with ethylacetate, and sequentially washed with water and salt water, excess water was removed using magnesium sulfate, followed by column chromatography, thereby obtaining 8.0 g of the title compound (66.6%).
$^1$H-NMR (300 MHz, CDCl$_3$): δ 7.84 (d, 2H, J=8.3 Hz), 7.37 (t, 2H, J=8.2 Hz & 7.9 Hz), 6.84 (d, 2H, J=7.6 Hz), 4.05 (d, 4H, J=5.4 Hz), 1.86 (m, 2H), 1.60-1.51 (m, 10H), 1.38-1.33 (m, 8H), 0.99-0.88 (m, 10H); Mass: m/z 384.

Synthesis of 1,5-bis-(2-ethylhexyloxy)-2,6-dibromonaphthalene

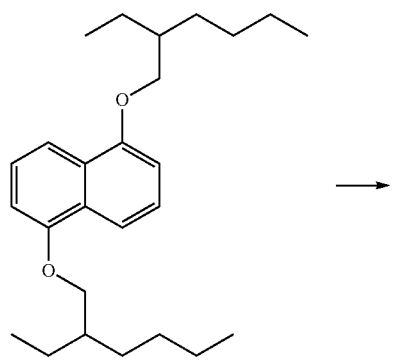

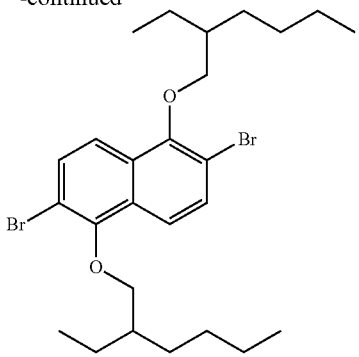

5.0 g of 1,5-bis-(2-ethylhexyloxy)naphthalene (13.0 mmol) was dissolved in 100 mL of methylene chloride, and a solution obtained by dissolving 4.2 g of bromine (26.3 mmol) in 50 mL of dichloromethane was slowly added thereto at 0° C. for 1 hour. Then, a temperature was raised to room temperature, and the mixture was stirred for 3 hours. The remaining bromine was removed from a hood, and the solvent was distilled under reduced pressure, followed by separation of column, thereby obtaining 5.5 g of the title compound (78.0%).
$^1$H-NMR (300 MHz, CDCl$_3$): δ 7.71 (d, 2H, J=8.9 Hz), 7.58 (d, 2H, J=8.9 Hz), 3.92 (d, 4H, J=5.8 Hz), 1.86 (m, 2H), 1.51-1.33 (m, 6H), 1.32-1.10 (m, 10H), 0.98-0.88 (m, 12H); Mass: m/z 542.

Synthesis of 1,5-bis-(2-ethylhexyloxy)naphthalene-2,6-dicarbaldehyde

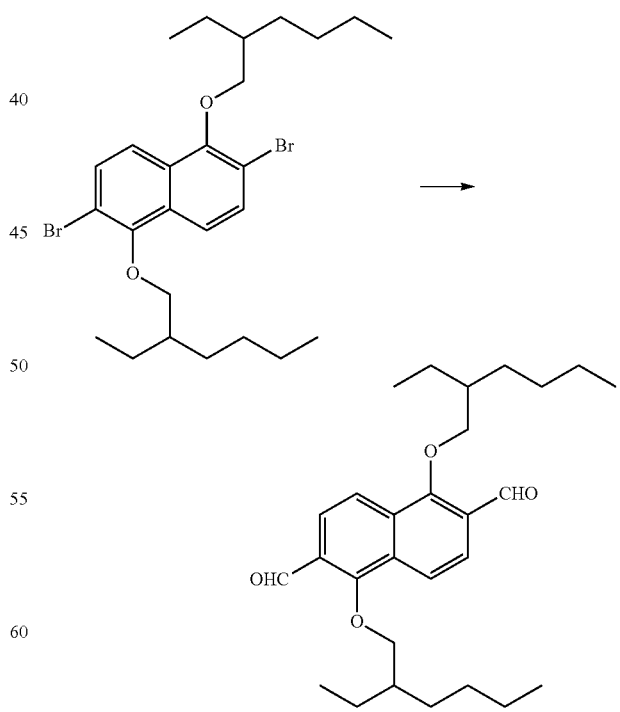

After 1.0 g of 1,5-bis-(2-ethylhexyloxy)-2,6-dibromonaphthalene (1.8 mmol) was dissolved in 20 mL of tetrahydrofuran (THF), a temperature was raised to −78° C., and n-butyl lithium was slowly added thereto for 30 minutes. The mixture was stirred at −78° C. for 2 hours, and then 0.46 g of DMF (6.3 mmol) was slowly added thereto for 10 minutes and further stirred for 30 minutes. After a temperature was raised to room temperature and the reactant was stirred for 1 hour, the reaction was terminated by cool water, and the resultant was extracted with ethylacetate, followed by distillation under reduced pressure and column chromatography, thereby obtaining 1.1 g of the title compound (45.0%).

$^1$HNMR (400 MHz, CDCl$_3$): δ10.61 (s, 2H), 8.06 (d, 2H, J=8.8 Hz), 7.97 (d, 2H, J=8.8 Hz), 4.08 (d, 4H, J=5.9 Hz), 1.97 (m, 2H), 1.71-1.55 (m, 7H), 1.41-1.36 (m, 9H), 1.05-0.93 (m, 12H).

Synthesis of
1,5-bis-(2-ethylhexyloxy)-2,6-(N,N-dimethyl ethylenediamine) naphthalene

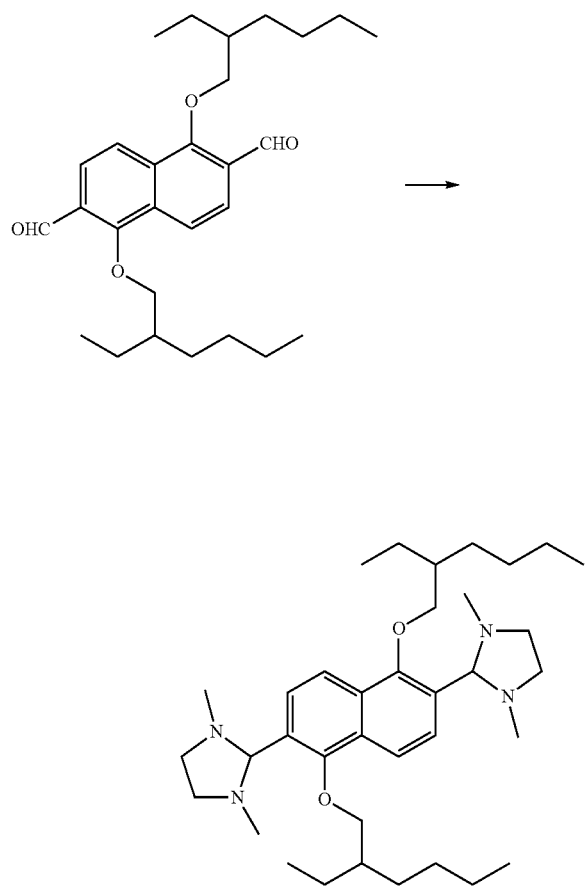

1.3 g of 1,5-bis-(2-ethyl hexyloxy)naphthalene-2,6-dicarbaldehyde (2.9 mmol) was dissolved in 20.0 mL of ethanol and stirred for 1 hour. After 0.66 g of N,N-dimethylethylene diamine (7.5 mmol) was added thereto and stirred at 25° C. for 24 hours, the solvent was removed by distillation under reduced pressure, followed by column chromatography, thereby obtaining 1.5 g of the title compound (87.7%).

$^1$HNMR (400 MHz, CDCl$_3$): δ7.85 (d, 2H J=8.8 Hz), 7.73 (d, 2H J=8.8 Hz), 3.98 (s, 2H), 3.82 (d, 4H J=5.9 Hz), 3.42 (q, 4H, J=1.8 Hz, 4.8 Hz & 3.6 Hz), 2.62 (q, 4H, J=1.8 Hz, 4.6 Hz & 3.6 Hz), 2.24 (s, 12H), 1.89 (m, 2H), 1.64-1.52 (m, 8H), 1.39-1.33 (m, 8H), 1.00-0.89 (m, 12H).

Synthesis of 3,7-dibromo-1,5-bis(2-ethylhexyloxy)-naphthalene-2,6-dicarbaldehyde

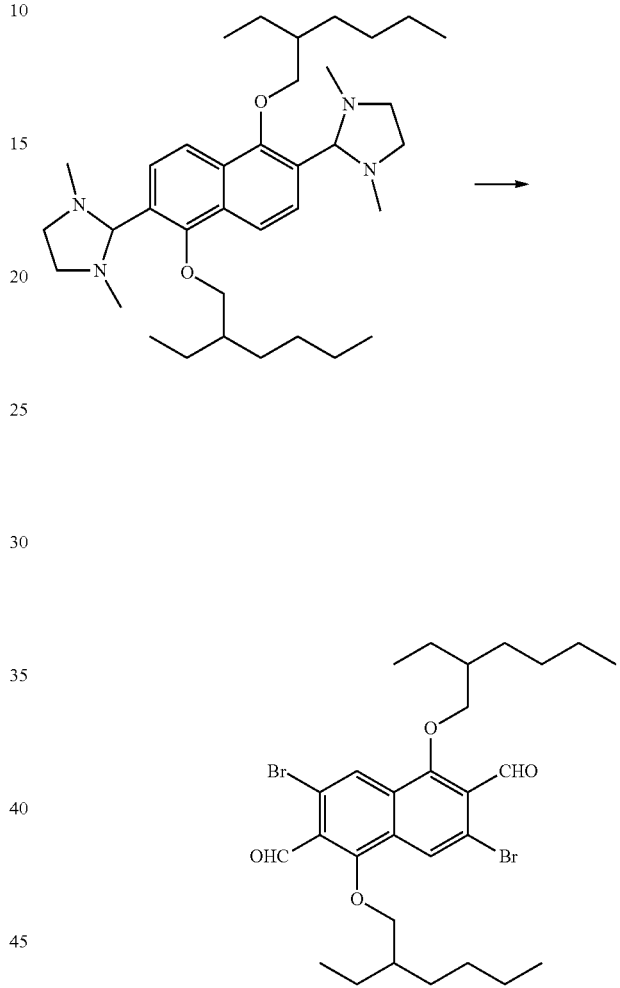

1.0 g of 1,5-bis-(2-ethylhexyloxy)-2,6-(N,N-dimethylethylenediamine) naphthalene (1.7 mmol) was dissolved in 40 mL of diethylether and stirred for 1 hour. Then, 0.67 g of tert-butyl lithium (10.4 mmol) was slowly added thereto at −40° C. for 30 minutes and stirred for 30 minutes. After the reaction mixture was stirred at −20° C. for 7 hours, a temperature was lowered to −78° C., and 3.4 g of 1,2-dibromo tetrachloroethane (10.4 mmol) dissolved in 30.0 mL of diethylether at 0° C. was slowly added thereto using a cylinder. The reaction mixture was stirred at 0° C. for 1 hour and stirred again at 25° C. for 15 hours. After confirming completion of the reaction through thin layer chromatography (TLC), 100 mL of 2M aqueous hydrochloric acid was added at 0° C. and stirred for 1 hour, followed by stirring at 25° C. for 4 hours. An organic layer was separated and sequentially washed with water and salt water, and excess moisture was removed using magnesium sulfate, followed by column chromatography, thereby obtaining 0.25 g of the title compound (25.0%).

¹H-NMR (400 MHz, CDCl₃): δ10.52 (s, 2H), 8.24 (s, 2H), 4.02 (d, 4H, J=5.8 Hz), 1.86 (m, 2H), 1.63-1.53 (m, 6H), 1.42-1.37 (m, 10H), 1.05-0.94 (m, 12H).

Synthesis of 5,10-bis(2-ethylhexyloxy)-1,6-dithia-dicyclopenta[b,g]naphthalene-2,7-dicarboxylic acid diethyl ester

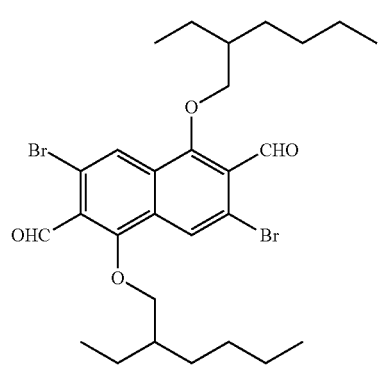

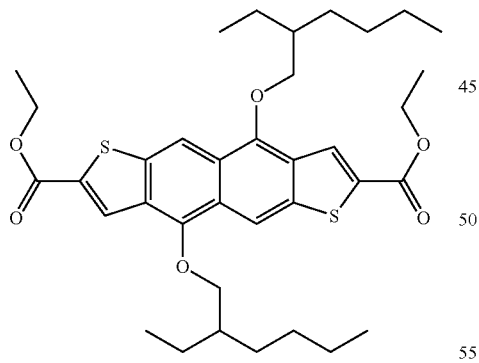

0.015 g of sodium (0.7 mmol) was added to 10 mL of anhydrous ethanol and stirred for 30 minutes. 0.087 g of ethyl-2-mercaptoacetate (0.7 mmol) was slowly added thereto at 0° C. After the mixture was stirred at 0° C. for 30 minutes, ethanol was diluted, and 0.2 g of 3,7-dibromo-1,5-bis(2-ethylhexyloxy)-naphthalene-2,6-dicarbaldehyde (0.3 mmol) was added thereto and stirred for 1 hour. The reaction mixture was further refluxed and stirred for 16 hours, and then solvent was removed, followed by column chromatography, thereby obtaining 0.125 g of the title compound (56%).

¹H-NMR (400 MHz, CDCl₃): δ8.53 (s, 2H), 8.29 (s, 2H), 4.51 (q, 4H, J=7.0 Hz, 7.1 Hz & 7.0 Hz), 4.25 (d, 4H, J=5.6 Hz), 2.02 (m, 2H), 1.97-1.52 (m, 10H), 1.42-1.37 (m, 12H), 1.05-0.88 (m, 12H).

Synthesis of 5,10-bis(2-ethylhexyloxy)-1,6-dithia-dicyclopenta[b,g]naphthalene-2,7-dicarboxylic acid

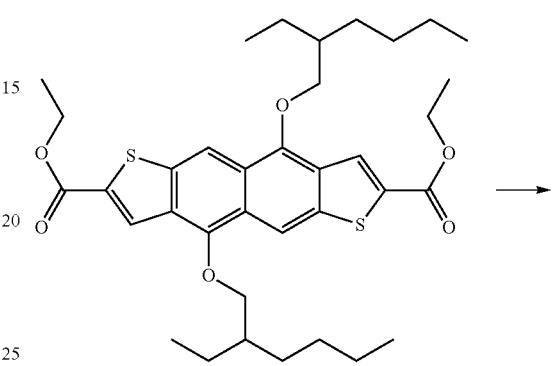

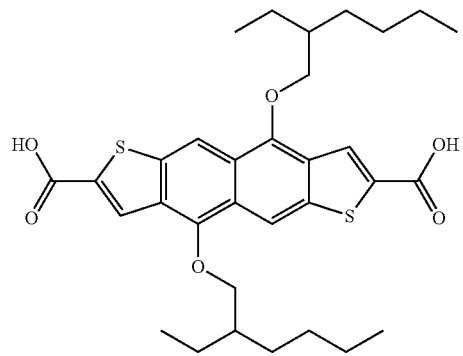

0.06 g of 5,10-bis(2-ethylhexyloxy)-1,6-dithia-dicyclopenta[b,g]naphthalene-2,7-dicarboxylic acid diethyl ester (0.009 mmol) was dissolved in 0.5 mL of THF:Methanol (1:1), and 0.2 mL of water and 0.01 g of lithium hydroxide (0.04 mmol) were added thereto and stirred at room temperature for 8 hours. Again, the mixture was further stirred at 50° C. for 8 hours, the solvent was removed, and a temperature was lowered to 0° C., and the resultant was acidified by 2N HCl solution, thereby obtaining 0.04 g of the title compound (74.0%).

¹H-NMR (400 MHz, DMSO-d₆): δ8.32 (s, 2H), 7.97 (s, 2H), 4.08 (d, 4H, J=5.2 Hz), 1.86 (m, 2H), 1.65-1.40 (m, 8H), 1.32-1.29 (m, 8H), 1.05-0.88 (m, 12H). Mass (EI): m/z 584

Synthesis of 4,9-bis(2-ethylhexyloxy)-1,6-dithia-dicyclopenta[b,g]naphthalene

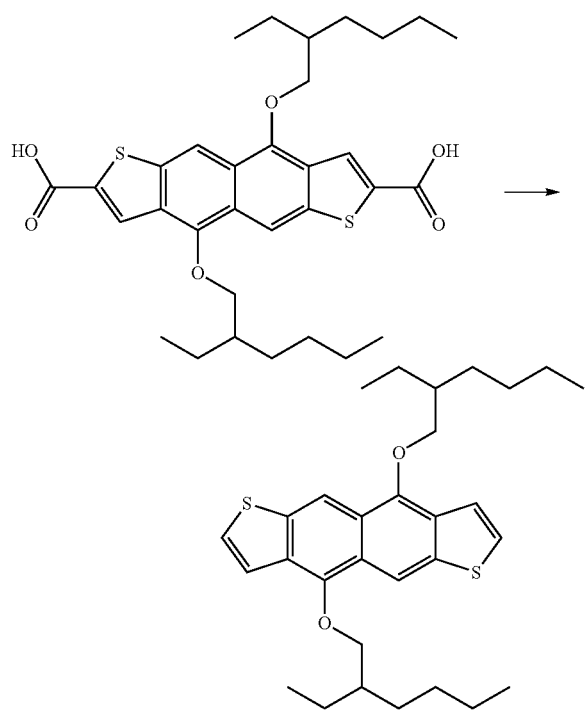

0.02 g of 5,10-bis(2-ethylhexyloxy)-1,6-dithia-dicyclopenta[b,g]naphthalene-2,7-dicarboxylic acid (0.003 mmol) was dissolved in 0.5 ml, of quinoline. 0.09 g of Cu (0.01 mmol) was added to the reaction solution and stirred at 180° C. for 8 hours. After a temperature was lowered, ethylacetate was added thereto at room temperature, and copper was filtered and removed. 2N Hal was added to an ethylacetate layer and sequentially washed with water and salt water, followed by distillation under reduced pressure and column chromatography, thereby obtaining 12 mg of the title compound (70%).

¹H-NMR (400 MHz, CDCl₃): δ8.52 (s, 2H), 7.51 (d, 2H, J=5.8 Hz), 7.40 (d, 2H, J=5.7 Hz), 4.13 (d, 4H, J=5.7 Hz), 1.88 (m, 2H), 1.58-1.5 (m, 7H), 1.48-1.41 (m, 9H), 1.07-0.97 (m, 12H).

¹³C-NMR (500 MHz, CDCl₃): δ149.7, 138.3, 130.4, 127.3, 124.7, 120.3, 110.8, 78.4, 41.1, 30.6, 29.3, 24.0, 23.3, 14.3, 11.4

MS (EI): m/z 496

Elemental Analysis Calcd. $C_{30}H_{40}O_2S_2$: C, 72.53; H, 8.12; S, 12.91%. Found: C, 72.46; H, 8.44; S, 12.92%.

Example 2

Synthesis of 4,9-bis(2-butyloctyloxy)-1,6-dithia-dicyclopenta[b,g]naphthalene 0.12 g of the title compound (67%) was obtained by the same method as in Example 1 except for using 2-butyloctyl bromide instead of 2-ethylhexyl bromide at the time of synthesizing 1,5-bis-(2-ethylhexyloxy)naphthalene.

¹H-NMR (300 MHz, CDCl₃): δ 8.54 (s, 2H), 7.48 (d, 2H, J=5.8 Hz), 7.35 (d, 2H, J=5.7 Hz), 4.11 (d, 4H, J=5.7 Hz), 1.96 (m, 2H), 1.72 (m, 4H), 1.57 (m, 4H), 1.43 (m, 24H), 0.98-0.88 (m, 12H)

¹³CNMR (75 MHz, CDCl₃): δ149.64, 138.35, 130.43, 127.17, 124.68, 120.26, 110.80, 78.42, 39.62, 32.10, 31.49, 31.19, 29.97, 29.40, 27.14, 23.33, 22.89, 14.35, 14.30.

EI Mass: mass calculated for $C_{38}H_{56}O_2S_2$, 608.37. Found 608.

Example 3

Synthesis of poly(4,9-bis((2-butyloctyl)oxy)naphtho[2,3-b:6,7-b']dithiophene-2-ethyl-1-(thieno[3,4-b]thiophen-2-yl)hexan-1-one) (PNDTTT)

Synthesis of (4,9-bis((2-butyloctyl)oxy)naphtho[2,3-b:6,7-b']dithiophene-2,7-diyl)bis(trimethylstannane)

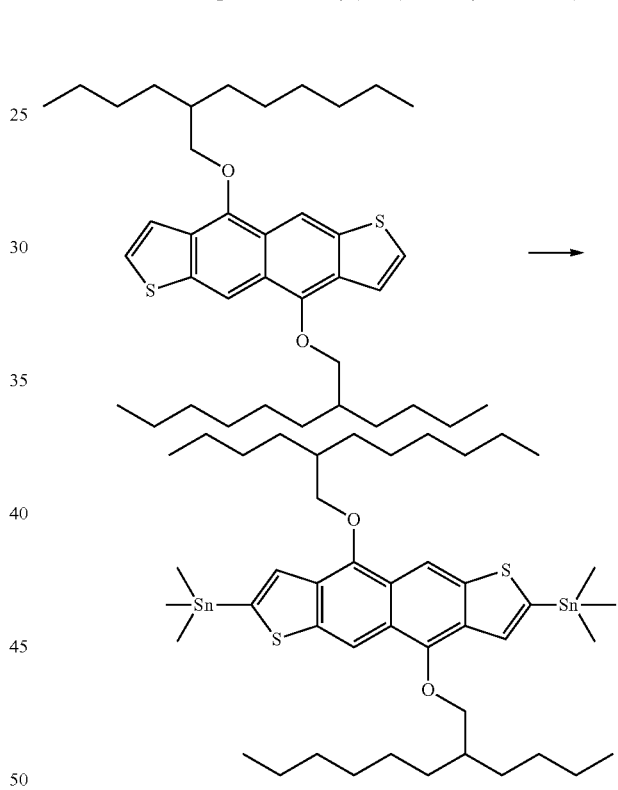

A solution in which 0.48 g of 4,9-bis(2-butyloctyloxy)-1,6-dithia-dicyclopenta[b,g]-naphthalene (0.78 mmol) prepared in Example 2 was dissolved in 20 mL of dry THF was cooled to −78° C., 1.9 mL of n-butyllithium (2.5M solution in hexane, 4.72 mmol) was added thereto. The reaction solution was stirred for 30 minutes and then stirred again at room temperature for 30 minutes. The reaction solution was cooled to −78° C. again, and 4.72 mL of Me₃SnCl (1M solution in hexane, 4.72 mmol) was slowly dropped therein. After the reaction solution was stirred again for 30 minutes, a temperature of the reaction solution was raised to room temperature, and the reaction solution was stirred for 12 hours. Water was added to the reaction solution, and a solvent layer was separated. The separated solvent layer was condensed, diluted with hexane, washed with distilled water, dried over Na₂SO₄, followed by filtering. Then, the obtained filtrate was condensed. The condensed filtrate was recrystallized using isopropanol, thereby obtaining 0.5 g of the title compound (68%) as a yellow solid.

$^1$H NMR (300 MHz, CDCl$_3$, ppm): δ 8.53 (s, 2H), 7.58 (d, 2H, J=5.8 Hz), 4.15 (d, 4H, J=5.7 Hz), 2.00 (m, 2H), 1.74 (m, 4H), 1.60 (m, 3H), 1.45 (m, 15H), 1.36 (m, 10H), 0.99-0.89 (m, 12H), 0.46 (t, 18H, J=28.7 Hz);

$^{13}$C NMR (75 MHz, CDCl$_3$, ppm): δ148.86, 142.81, 142.22, 131.93, 128.05, 124.39, 110.13, 78.39, 39.70, 32.16, 31.66, 31.34, 30.04, 29.50, 27.27, 23.37, 22.93, 14.38, 14.31;

EI Mass: calcd for $C_{44}H_{72}O_2S_2Sn_2$, 934.59. found 934.

Synthesis of poly(4,9-bis((2-butyloctyl)oxy)naphtho[2,3-b:6,7-b']dithiophene-2-ethyl-1-(thieno[3,4-b]thiophen-2-yl)hexan-1-one) (PNDTTT)

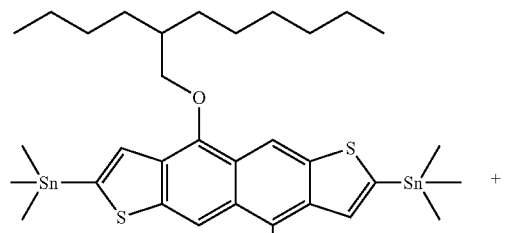

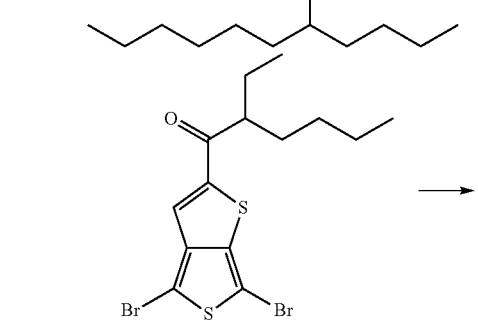

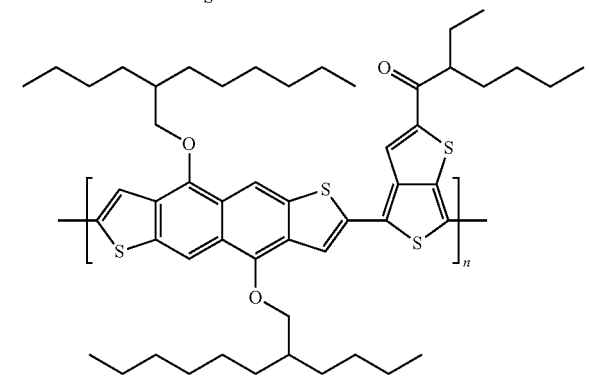

A reaction mixture obtained by dissolving 291 mg of 4,9-bis((2-butyloctyl)oxy)naphtho[2,3-b:6,7-b']dithiophene-2,7-diyl)bis(trimethyl-stannane) (0.31 mmol), 131 mg of 1-(4,6-dibromothieno[3,4-b]thiophen-2-yl)-2-ethylhexan-1-one (0.31 mmol), and 25 mg of Pd(Ph$_3$)$_4$ (0.02 mmol) in a mixed solution of 12 mL of toluene and 3 mL of DMF was stirred at 120° C. for 24 hours. After cooling the reaction solution, when 150 mL of methanol was added thereto, a precipitate was generated. After the produced solid was filtered and dissolved using a minimal amount of chloroform, the result-ant was reprecipitated by adding 150 mL of methanol. After the precipitate produced after stirring for 5 hours was put into a Soxhlet thimble and extracted with methanol for 24 hours, with acetone for 24 hours, with hexane for 2 hours, finally, the resultant was recovered using chloroform. The recovered chloroform solution was condensed and precipitated with methanol, followed by filtering, thereby obtaining 210 mg of the title compound (76%) as a dark blue solid.

Mn=21,408; Mw=68,877; PDI=3.2;

Example 4

Synthesis of poly[(4,9-bis((2-ethylhexyl)oxy)naphtho[2,3-b:6,7-b']dithiophene) (heptadecan-9-yl thieno[3,4-b]thiophene-2-carboxylate}]

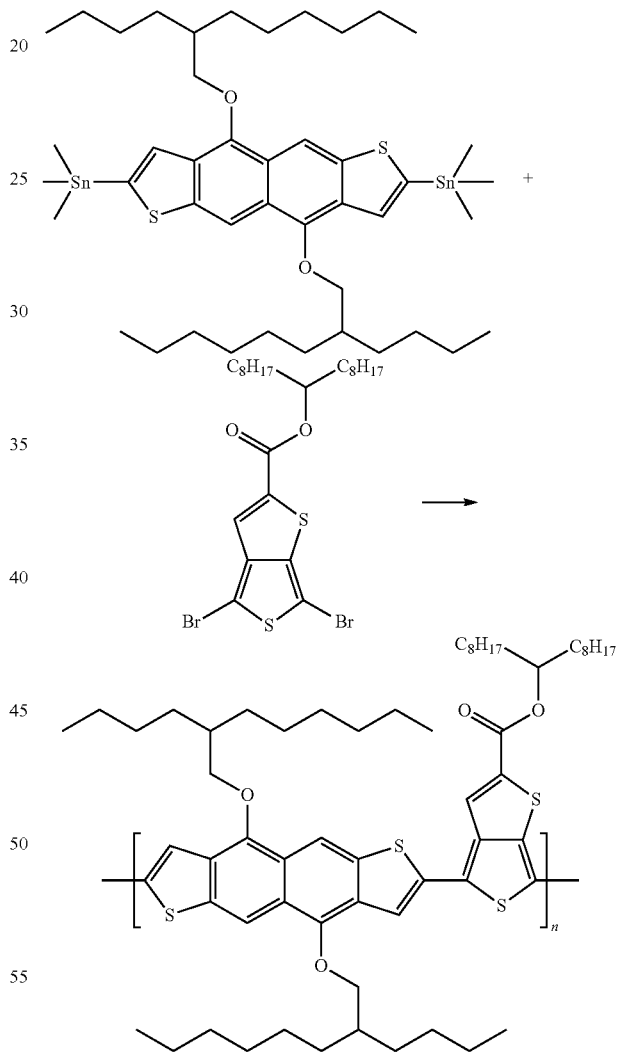

The title compound was synthesized by the same method as in Example 3 except for using 4,9-bis(2-ethylhexyloxy)-1,6-dithia-dicyclopenta[b,g]naphthalene synthesized in Example 1 instead of the compound synthesized in Example 2 and using heptadecan-9-yl4,6-dibromothieno[3,4-b]thiophene-2-carboxylate instead of 1-(4,6-dibromothieno[3,4-b]thiophen-2-yl)-2-ethylhexan-1-one.

Mn=22,116; Mw=53,440; PD1=2.4;

Example 5

Synthesis of poly [(4,9-bis((2-butyloctyl)oxy)naphtho[2,3-b:6,7-b']dithiophene) (2-ethylhexyl 3-fluorothieno[3,4-b]thiophene-2-carboxylate)]

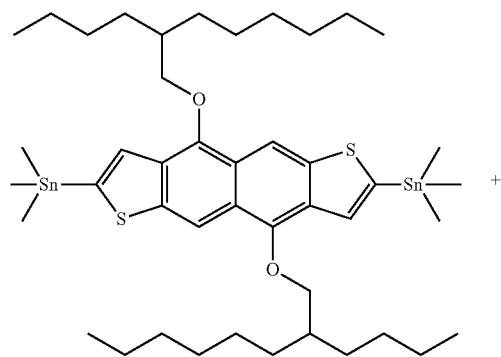

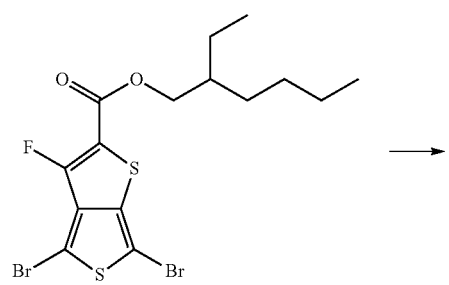

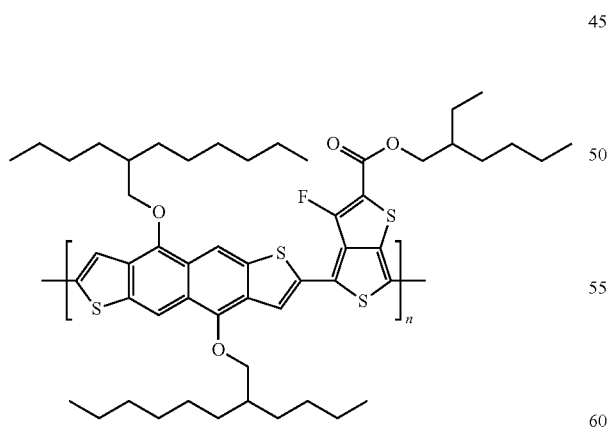

The title compound was synthesized by the same method as in Example 3 except for using 2-ethylhexyl 4,6-dibromo-3-fluorothieno[3,4-b]thiophene-2-carboxylate instead of 1-(4,6-dibromothieno[3,4-b]thiophen-2-yl)-2-ethylhexan-1-one.

Mn=40,201; Mw=112,800; PDI=2.8;

Example 6

Synthesis of poly[1-(4,9-bis((2-butyloctyl)oxy)naphtho[2,3-b:6,7-b']dithiophen-2-yl)-5-octyl-4H-thieno[3,4-c]pyrrole-4,6(5H)-dione]

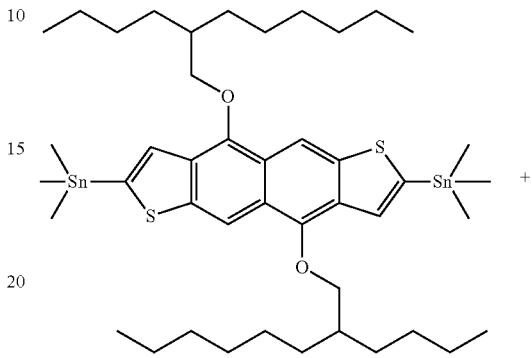

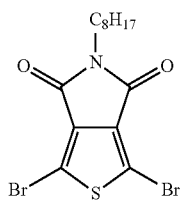

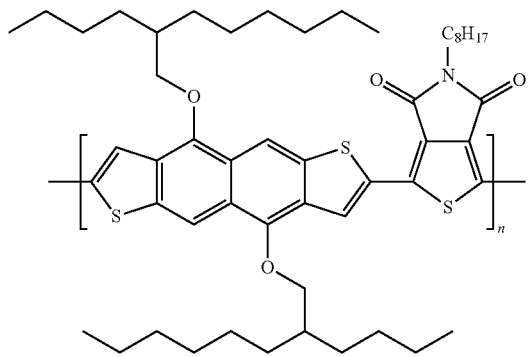

The title compound was synthesized by the same method as in Example 3 except for using 1,3-dibromo-5-octyl-5H-thieno[3,4-c]pyrrole-4,6-dione instead of 1-(4,6-dibromothieno[3,4-b]thiophen-2-yl)-2-ethylhexan-1-one.

Mn-10,115; Mw=29,136; PDI=2.88;

Example 7

Synthesis of poly[2-ethylhexyl-4-(4,9-bis((2-butyloctyl)oxy)naphtho[2,3-b:6,7-b']dithiophen-2-yl)selenopheno[3,4-b]thiophene-2-carboxylate]

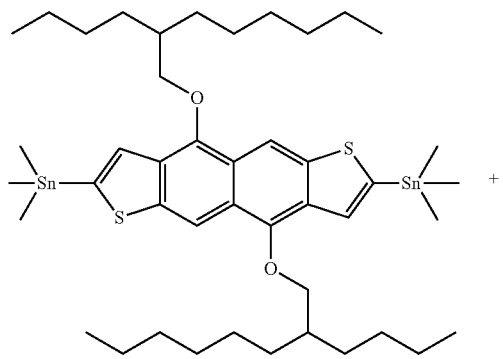

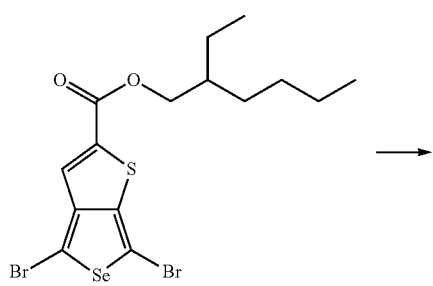

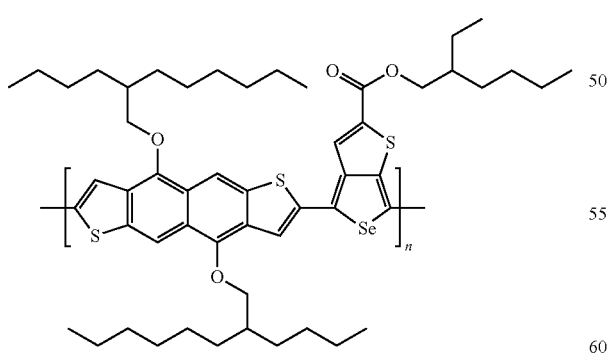

The title compound was synthesized by the same method as in Example 3 except for using 2-ethylhexyl 4,6-dibromoselenopheno[3,4-b]thiophene-2-carboxylate instead of 1-(4,6-dibromothieno[3,4-b]thiophen-2-yl)-2-ethylhexan-1-one.

$Mn=24,095$; $Mw=94,205$; $PDI=3.91$;

Example 8

Synthesis of poly[1-(4,9-bis((2-butyloctyl)oxy)naphtno[2,3-b:6,7-b']dithiophen-2-yl)-5-(heptadecan-9-yl)-4H-thieno[3,4-c]pyrrole-4,6(5H)-dione]

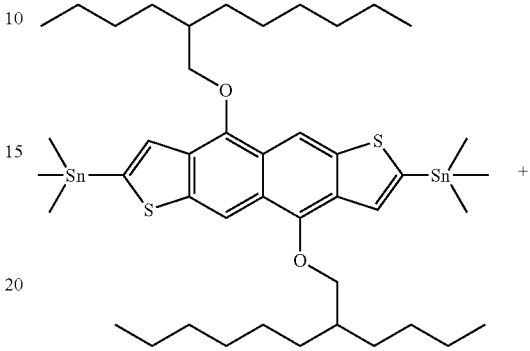

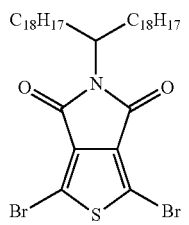

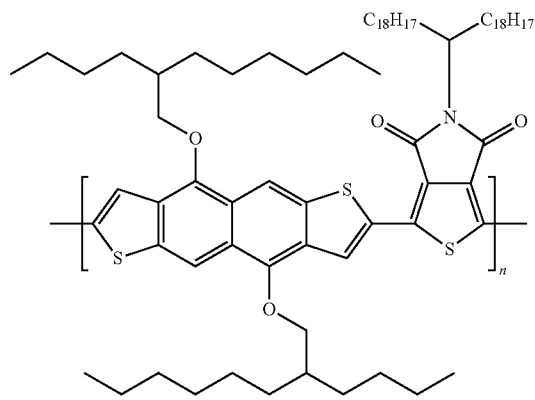

The title compound was synthesized by the same method as in Example 3 except for using 1,3-dibromo-5-(heptadecan-9-yl)-5H-thieno[3,4-c]pyrrole-4,6-dione instead of 1-(4,6-dibromothieno[3,4-b]thiophen-2-yl)-2-ethylhexan-1-one.

$Mn=24,119$; $Mw=50,921$; $PDI=2.11$;

Example 9

Synthesis of poly[1-(4,9-bis((2-butyloctyl)oxy)naphtho[2,3-b:6,7-b']dithiophen-2-yl)-5-(2-butyloctyl)-4H-thieno[3,4-c]pyrrole-4,6(5H)-dione]

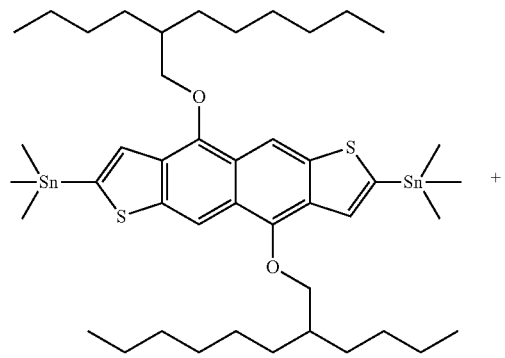

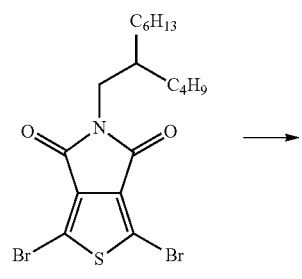

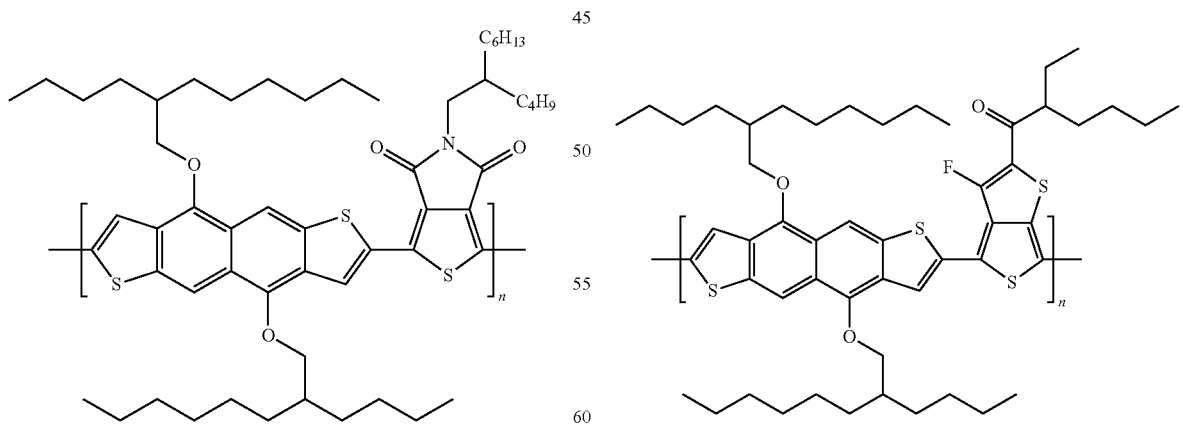

The title compound was synthesized by the same method as in Example 3 except for using 1,3-dibromo-5-(2-butyloctyl)-5H-thieno[3,4-c]pyrrole-4,6-dione instead of 1-(4,6-dibromothieno[3,4-b]thiophen-2-yl)-2-ethylhexan-1-one.

Mn=60,062; Mw=183,970; PDI=3.06;

Example 10

Synthesis of poly[1-(4-(4,9-bis((2-butyloctyl)oxy) naphtho[2,3-b:6,7-b']-dithiophen-2-yl)-3-fluorothieno[3,4-b]thiophen-2-yl)-2-ethylhexan-1-one]

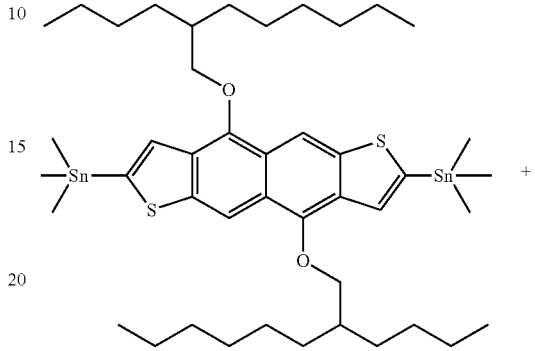

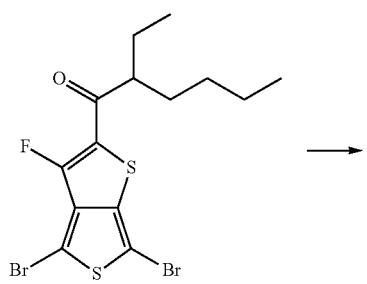

The title compound was synthesized by the same method as in Example 3 except for using 1-(4,6-dibromo-3-fluorothieno[3,4-b]thiophen-2-yl)-2-ethylhexan-1-one instead of 1-(4,6-dibromothieno[3,4-b]thiophen-2-yl)-2-ethylhexan-1-one.

Mn=61,018; Mw=136,054; PDI=2.23;

Example 11

Synthesis of poly[(4,9-bis((2-butyloctyl)oxy)naphtho[2,3-b:6,7-b']dithiophene](4,7-bis(4-(2-ethylhexyl)thiophen-2-yl)-[1,2,5]thiadiazolo[3,4-c]pyridine)

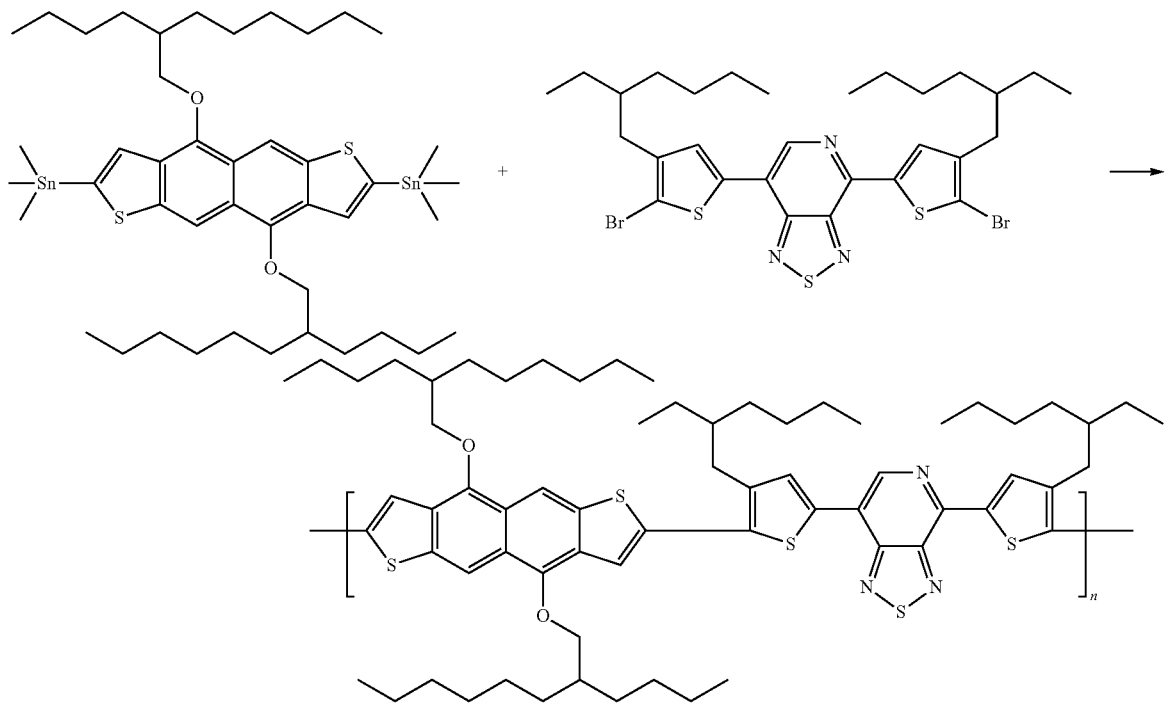

The title compound was synthesized by the same method as in Example 3 except for using 4,7-bis(5-bromo-4-(2-ethylhexyl)thiophen-2-yl)-[1,2,5]thiadiazolo[3,4-c]pyridine instead of 1-(4,6-dibromothieno[3,4-b]thiophen-2-yl)-2-ethylhexan-1-one.

Mn=4,372; Mw=7,184; PDI=1.64;

Example 12

Manufacturing of Photovoltaic Device

A composite solution (polymer prepared in Examples 3 to 11: $PC_{71}BM$=1:0.5 to 4.0 (weight ratio)) of the polymer obtained in the Examples 3 to 11 and [6,6]-phenyl C71 butyric acid methyl ester ($PC_{71}BM$) was prepared using 1,2-dichlorobenzene or chlorobenzene as a solvent. A concentration was controlled at 1.0 to 2.0 weight %. In addition, 1,8-diiodooctane was used at a weight ratio of 1 to 5%. A polymer photovoltaic device containing the polymer in Examples 3 to 11 was manufactured so as to have a typical sandwich structure (ITO/PEDOT:PSS/active layer/LiF or $TiO_x$/Al). A glass substrate coated with indium tin oxide (ITO) was washed by a general cleaning process, ultrasonic treatment in detergent, and cleaning with distilled water, acetone, and 2-propanol. After an ITO surface was exposed to ozone for 10 minutes, a poly(3,4-ethylenedioxythiophene): polystyrene sulfanate (PEDOT: PSS, Baytron P) layer having a thickness of 45 nm was spin coated on the ITO substrate. The PEDOT:PSS layer was baked on a hot plate at 140° C. for 10 minutes. An active layer was formed by spin coating the composite solution dissolved in advance after filtering using a 0.45 μm (PTFE) syringe filter. A LiF electrode having a thickness of 0.7 nm or a Ca electrode having a thickness of 2.0 nm and an Al cathode having a thickness of 100 nm as the uppermost electrode were deposited on the obtained device structure body in a thermal distiller under vacuum ($3\times10^{-6}$ torr), thereby completing the photovoltaic device.

Current density-voltage (J-V) characteristics of all of the polymer photovoltaic cells were measured under solar simulated illumination of 100 mW/cm² (AM 1.5 G) by using an Oriel 1000 W solar simulator. Electric data was recorded using a Keithley 236 source-measure unit, and all of the characteristics were measured at room temperature. The illuminance was compensated by employing a standard Si photodiode detector (PV measurements Inc.) calibrated at National Renewable Energy Laboratory (NREL). Incident photon-to-current conversion efficiency (IPCE) was measured as a function of the wavelength in a range of 360 to 800 nm (PV Measurements Inc) using a halogen lamp as a light source and calibrated using a standard silicon photodiode. A thickness of the thin film was measured using a KLA Tencor Alpha-step IQ surface profilometer with an accuracy of ±1 nm.

Measurement results of Example 12 were shown in Table 1. That is, open circuit voltage ($V_{oc}$), short-circuit current density ($J_{SC}$), fill factor (FF), and a photovoltaic parameter of overall conversion efficiency (η) were shown in Table 1.

The fill factor and the overall conversion efficiency among electro-optical characteristics were calculated by the following Equations 1 and 2.

$$\text{fill factor} = \frac{(V_{mp} \times I_{mp})}{(V_{oc} \times I_{sc})} \qquad [\text{Equation 1}]$$

(Where, $V_{mp}$ is a voltage value at the maximum power point, $I_{mp}$ is current density, $V_{oc}$ is open circuit voltage, and $I_{sc}$ is short-circuit current.)

$$\text{energy conversion efficiency}(\%) = \text{fill factor} \times \frac{(J_{sc} \times V_{oc})}{100} \quad \text{[Equation 2]}$$

(Where, $J_{sc}$ is short-circuit current density, and $V_{oc}$ is open circuit voltage.)

An optical band gap from UV spectrum was low (1.60 to 1.78), such that an increase in the open circuit voltage may be generally expected.

As a result of measuring the photoelectric conversion efficiency, it may be confirmed that the photoelectric conversion efficiency was tendentiously changed according to an intensity of electron-withdrawing effect of an acceptor group. That is, as shown in Table 1, as the intensity of the electro-withdrawing effect was increased in a substitution sequence (Example 4→Example 3→Example 10) of ester, ketone, and fluoro and ketone, which were substituents of the thienothiophene, the efficiency was sequentially increased.

In the cases of Examples 5 and 10, the same result was obtained due to the same reason. As known through comparison of Examples 4 and 7, it may be confirmed that in the case in which thiophene was substituted with selenophene in an acceptor backbone, charge mobility was increased. Comparing the results of measuring photoelectric conversion efficiency of Examples 6, 8, and 9 with each other, the photoelectric conversion efficiency was changed according to the bulkiness of the substituent of the acceptor group. That is, there was no large change in efficiency between Examples 6 and 8, but it may be estimated that proximity between polymer molecules was affected due to proximity of adjacent naphthalene-dithiophene with butyloctyloxy group. On the contrary, it may be confirmed that in the case of Example 9 in which proximity of adjacent naphthalene-dithiophene with butyloctyloxy group was prevented by introducing 2-butyloctyl group, the efficiency was increased.

Therefore, in a conductive polymer in which the naphthalene-dithiophene compound was introduced, energy conversion efficiency (%) was maximized through optimization of donor-acceptor combination, such that the polymer compound capable of having high energy conversion efficiency was prepared.

TABLE 1

| | Device results (of max PCE) | | | |
|---|---|---|---|---|
| | $V_{oc}$ (V) | $J_{sc}$ (mA/cm$^2$) | FF (%) | η (%) |
| Example 3 | 0.70 | 10.42 | 0.56 | 4.05 |
| Example 4 | 0.65 | 7.56 | 0.50 | 2.44 |
| Example 5 | 0.72 | 8.66 | 0.50 | 3.1 |
| Example 6 | 0.66 | 5.06 | 0.49 | 1.63 |
| Example 7 | 0.60 | 11.33 | 0.47 | 3.19 |
| Example 8 | 0.69 | 5.42 | 0.41 | 1.54 |
| Example 9 | 0.72 | 10.48 | 0.52 | 3.92 |
| Example 10 | 0.74 | 13.07 | 0.52 | 5.01 |
| Example 11 | 0.68 | 7.36 | 0.47 | 2.34 |

The invention claimed is:

1. An organic semiconductor compound represented by the following Chemical Formula 1

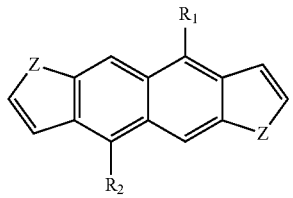

[Chemical Formula 1]

wherein, Z is S or Se; and
R$_1$ and R$_2$ each are independently (C$_1$-C$_{20}$)alkyl, (C$_1$-C$_{20}$)alkoxy, (C$_1$-C$_{20}$)alkylthio, or (C$_6$-C$_{20}$)ar(C$_1$-C$_{20}$)alkyl, and the alkyl and aralkyl are further substituted with at least one substituent selected from (C$_1$-C$_{20}$)alkyl, (C$_2$-C$_{20}$)alkenyl, (C$_2$-C$_{20}$)alkynyl, (C$_1$-C$_{20}$)alkoxy, amino groups, hydroxyl groups, halogen groups, cyano groups, nitro groups, trifluoromethyl groups, and silyl groups.

2. The organic semiconductor compound of claim 1, wherein R$_1$ and R$_2$ each are independently (C$_1$-C$_{20}$)alkyl or (C$_1$-C$_{20}$)alkoxy.

3. The organic semiconductor compound of claim 1, wherein Z is S.

4. A method for preparing an organic semiconductor compound represented by Chemical Formula 1, the method comprising:
introducing a protective group in a compound represented by the following Chemical Formula 2 to prepare a compound represented by Chemical Formula 3;
halogenating the compound represented by Chemical Formula 3 to prepare a compound represented by Chemical Formula 4;
reacting the compound represented by Chemical Formula 4 with a compound represented by Chemical Formula 5 to prepare a compound represented by Chemical Formula 6; and
preparing a compound represented by Chemical Formula 1 from the compound represented by Chemical Formula 6

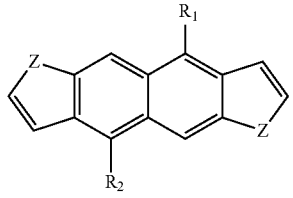

[Chemical Formula 1]

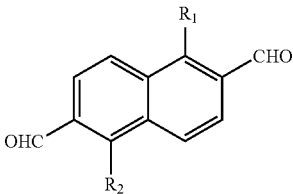

[Chemical Formula 2]

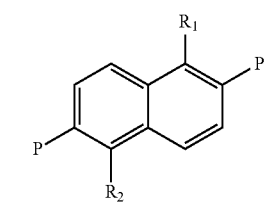

[Chemical Formula 3]

-continued

[Chemical Formula 4]

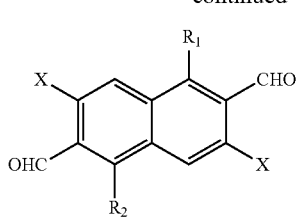

[Chemical Formula 5]

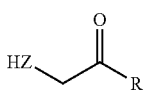

[Chemical Formula 6]

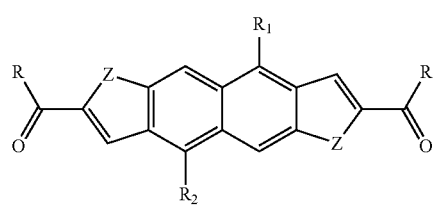

wherein, Z is S or Se;
$R_1$ and $R_2$ each are independently ($C_1$-$C_{20}$)alkyl, ($C_1$-$C_{20}$)alkoxy, ($C_1$-$C_{20}$)alkylthio, or ($C_6$-$C_{20}$)ar($C_1$-$C_{20}$)alkyl, and the alkyl and aralkyl are further substituted with at least one substituent selected from ($C_1$-$C_{20}$)alkyl, ($C_2$-$C_{20}$)alkenyl, ($C_2$-$C_{20}$)alkynyl, ($C_1$-$C_{20}$)alkoxy, amino groups, hydroxyl groups, halogen groups, cyano groups, nitro groups, trifluoromethyl groups, and silyl groups;
P is a protective group; X is a halogen; and
R is hydroxyl or ($C_1$-$C_{20}$)alkoxy.

5. The method of claim 4, further comprising:
preparing a compound represented by Chemical Formula 8 from a compound represented by Chemical Formula 7; and
preparing a compound represented by Chemical Formula 2 from a compound represented by Chemical Formula 8

[Chemical Formula 7]

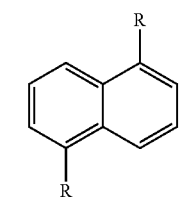

[Chemical Formula 8]

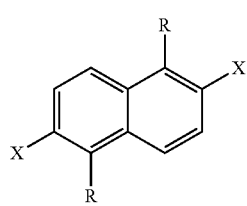

wherein, Z is S or Se; X is a halogen; and
R is hydroxyl or ($C_1$-$C_{20}$) alkoxy.

6. The method of claim 4, wherein the protective group is one selected from N,N-dimethylethylenediamine, 1,3-propanediol, 1,3-propanedithiol, and pinacol.

7. The method of claim 4, wherein the halogenating is performed using one selected from bromine, chlorine, N-bromosuccinimide, and 1,2-dibromotetrachloroethane.

8. The method of claim 4, wherein Z is S, and R is a ($C_1$-$C_{20}$)alkoxy.

9. A polymer compound including an organic semiconductor compound represented by the following Chemical Formula 1

[Chemical Formula 1]

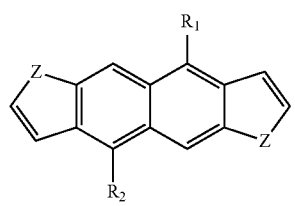

wherein, Z is S or Se; and
$R_1$ and $R_2$ each are independently ($C_1$-$C_{20}$)alkyl, ($C_1$-$C_{20}$)alkoxy, ($C_1$-$C_{20}$)alkylthio, ($C_6$-$C_{20}$)ar($C_1$-$C_{20}$)alkyl, and the alkyl and aralkyl are further substituted with at least one substituent selected from ($C_1$-$C_{20}$)alkyl, ($C_2$-$C_{20}$)alkenyl, ($C_2$-$C_{20}$)alkynyl, ($C_1$-$C_{20}$)alkoxy, amino groups, hydroxyl groups, halogen groups, cyano groups, nitro groups, trifluoromethyl groups, and silyl groups.

10. The polymer compound of claim 9, wherein it is represented by the following Chemical Formula 11

[Chemical Formula 11]

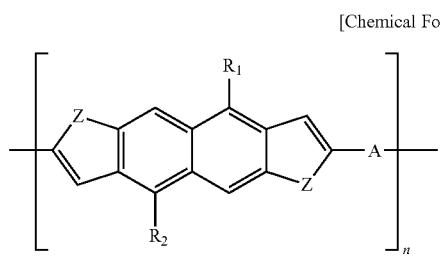

wherein, A is ($C_6$-$C_{20}$)arylene or ($C_3$-$C_{20}$)heteroarylene,
Z is S or Se;
$R_1$ and $R_2$ each are independently ($C_1$-$C_{20}$)alkyl, ($C_1$-$C_{20}$)alkoxy, ($C_1$-$C_{20}$)alkylthio, or ($C_6$-$C_{20}$)ar($C_1$-$C_{20}$)alkyl, and the alkyl and aralkyl are further substituted with at least one substituent selected from ($C_1$-$C_{20}$)alkyl, ($C_2$-$C_{20}$)alkenyl, ($C_2$-$C_{20}$)alkynyl, ($C_1$-$C_{20}$)alkoxy, amino groups, hydroxyl groups, halogen groups, cyano groups, nitro groups, trifluoromethyl groups, and silyl groups; and
n is an integer of 1 to 500.

11. The polymer compound of claim 10, wherein A is at least one selected from compounds having the following structures

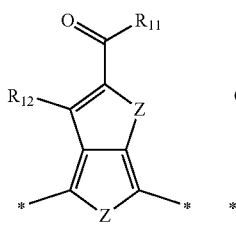 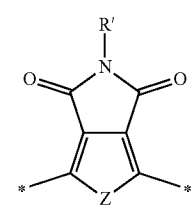

-continued

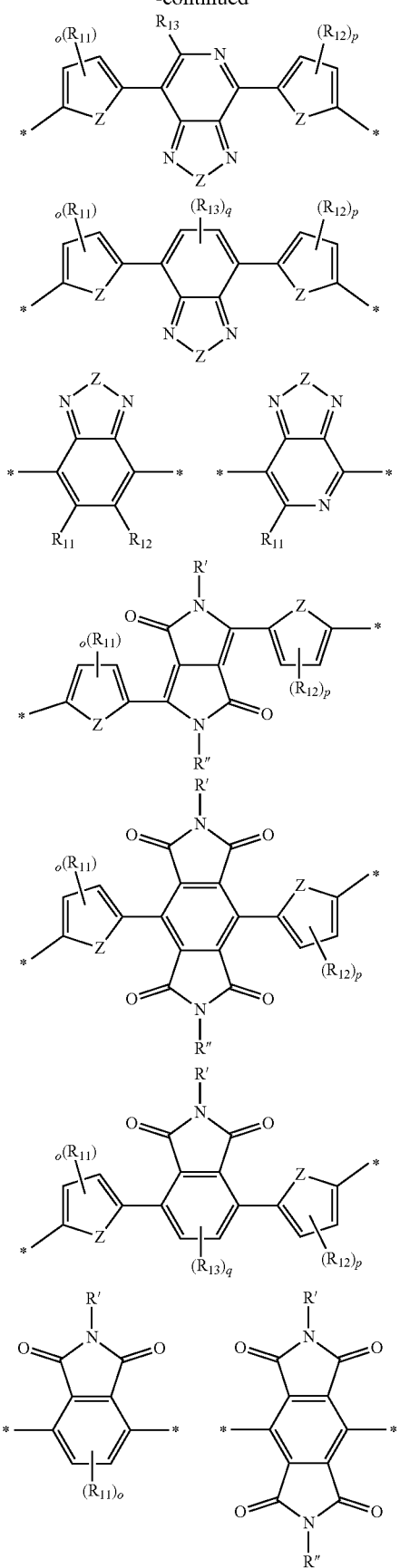

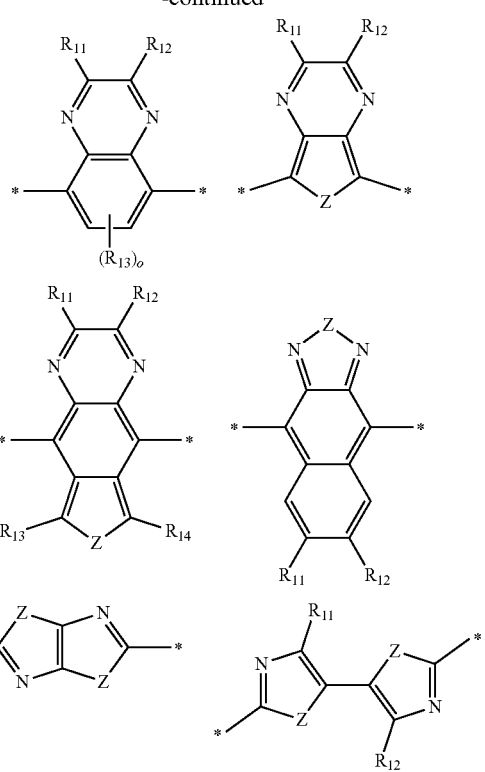

wherein, Z is S or Se,

R' and R" each are independently hydrogen, or $(C_1-C_{20})$ alkyl, $(C_6-C_{20})$aryl, $(C_3-C_{20})$heteroaryl, or $(C_6-C_{20})$ar$(C_1-C_{20})$alkyl, $R_{11}$ to $R_{14}$ each are independently hydrogen, halogen, a $(C_1-C_{20})$alkyl, $(C_1-C_{20})$alkoxy, or $(C_6-C_{20})$ar$(C_1-C_{20})$alkyl, the alkyl, aryl, heteroaryl, and aralkyl of R' and R" and the alkyl, alkoxy, and aralkyl of $R_{11}$ to $R_{14}$ are further substituted with at least one substituent selected from $(C_1-C_{20})$alkyl, $(C_2-C_{20})$alkenyl, $(C_2-C_{20})$alkynyl, $(C_1-C_{20})$alkoxy, amino groups, hydroxyl groups, halogen groups, cyano groups, nitro groups, trifluoromethyl groups, and silyl groups; and o, p, and q are integers of 1 to 2.

12. The polymer compound of claim 10, wherein the Chemical Formula 2 is selected from the following Structural Formulas

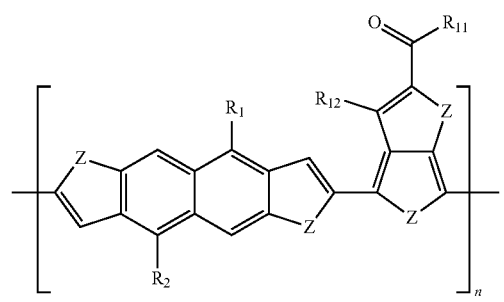

-continued

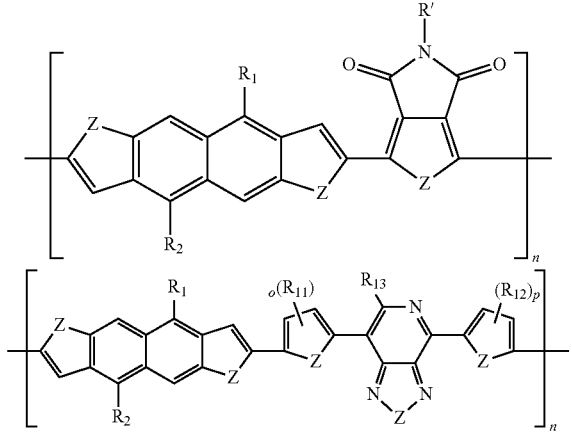

wherein, Z is S or Se,
R$_1$ and R$_2$ each are independently (C$_1$-C$_{20}$)alkyl, (C$_1$-C$_{20}$)alkoxy, (C$_1$-C$_{20}$)alkylthio, or (C$_6$-C$_{20}$)ar(C$_1$-C$_{20}$)alkyl, and the alkyl and aralkyl are further substituted with at least one substituent selected from (C$_1$-C$_{20}$)alkyl, (C$_2$-C$_{20}$)alkenyl, (C$_2$-C$_{20}$)alkynyl, (C$_1$-C$_{20}$)alkoxy, amino groups, hydroxyl groups, halogen groups, cyano groups, nitro groups, trifluoromethyl groups, and silyl groups;

R' is hydrogen, (C$_1$-C$_{20}$)alkyl, (C$_6$-C$_{20}$)aryl, (C$_3$-C$_{20}$)heteroaryl, or (C$_6$-C$_{20}$)ar(C$_1$-C$_{20}$)alkyl, R$_{11}$ to R$_{13}$ each are independently hydrogen, halogen, (C$_1$-C$_{20}$)alkyl, (C$_1$-C$_{20}$)alkoxy, or (C$_6$-C$_{20}$)ar(C$_1$-C$_{20}$)alkyl, the alkyl, aryl, heteroaryl, and aralkyl of R' and the alkyl, alkoxy, and aralkyl of R$_{11}$ to R$_{13}$ are substituted with at least one substituent selected from (C$_1$-C$_{20}$)alkyl, (C$_2$-C$_{20}$)alkenyl, (C$_2$-C$_{20}$)alkynyl, (C$_1$-C$_{20}$)alkoxy, amino groups, hydroxyl groups, halogen groups, cyano groups, nitro groups, trifluoromethyl groups, and silyl groups;

n is an integer of 1 to 500; and o and p are integers of 1 to 2.

13. An organic semiconductor device comprising the polymer compound of claim 9.

* * * * *